United States Patent [19]

Carr

[11] 4,118,507
[45] Oct. 3, 1978

[54] BENZODIOXINCARBOXAMIDE LIPOGENESIS INHIBITORS

[75] Inventor: John B. Carr, Modesto, Calif.
[73] Assignee: Shell Oil Company, Houston, Tex.
[21] Appl. No.: 778,535
[22] Filed: Mar. 17, 1977
[51] Int. Cl.$^2$ .......................................... A61K 31/335
[52] U.S. Cl. .................................................. 424/278
[58] Field of Search ........................................ 424/278

[56] References Cited
PUBLICATIONS

Koo et al., J. Am. Chem. Soc., 77, 5373 (1955).

Primary Examiner—Leonard Schenkman

[57] ABSTRACT

2,3-Dihydro-N-(2-propenyl)-1,4-benzodioxin-2-carboxamides inhibit lipogenesis in mammals.

2 Claims, No Drawings

BENZODIOXINCARBOXAMIDE LIPOGENESIS INHIBITORS

DESCRIPTION OF THE INVENTION

It has been found that lipogenesis is inhibited in mammals by 2,3-dihydro-N-(2-propenyl)-1,4-benzodioxin-2-carboxamides, described by the formula:

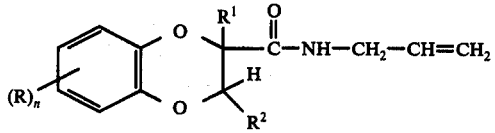
(I)

wherein $n$ is zero or one, R is halogen; nitro; amino; methylsulfonylamino; trifluoromethyl; alkyl or alkoxy of from one to six carbon atoms; cycloalkyl or cycloalkyloxy of from three to six carbon atoms; phenyl or phenoxy, or either of these substituted by one or two of one or more of alkyl of from one to six carbon atoms, halogen and nitro, and $R^1$ and $R^2$ each is hydrogen or alkyl of from one to four carbon atoms, at least one being hydrogen. By halogen is meant chlorine, fluorine, bromine and iodine, the middle halogens, bromine and chlorine, being preferred. Each alkyl moiety may be of straight-chain or branched-chain configuration.

Preferred of these compounds, because of their activity in inhibiting lipogenesis, are those wherein $n$ is zero or $n$ is one and R is middle halogen substituted at the 6-position of the ring structure; and $R^1$ and $R^2$ each is hydrogen.

In compounds of this class wherein $R^2$ is alkyl, the compounds can exist in the form of cis- and trans-isomers, referring to the spatial relationship of the carboxamide and alkyl moieties, and it has been found that whereas the cis- form when $R^2$ is alkyl inhibits lipogenesis, the trans- form is essentially inactive. Consequently, the invention contemplates only the cis-isomers of the compounds of Formula I wherein $R^2$ is alkyl.

Further, chirality exists in the compounds of Formula I due to the asymmetric structural configuration at the 2-position of the 2,3-dihydro-1,4-benzodioxan ring. As a result, two optical isomers, of the compounds of Formula I wherein $R^2$ is hydrogen and of the cis-configuration of the compounds of Formula I wherein $R^2$ is alkyl, exist. At the time this application is filed, no attempt has been made to separate and determine the lipogenesis inhibition activity of the individual optical isomers. Under the circumstances, the invention contemplates the individual optical isomers, as well as mixtures thereof.

For illustration, preparation of typical individual species of the genus defined by Formula I are described in the examples included hereinafter. Other typical, illustrative individual species of this genus are those wherein the respective moieties are:

| R | $R^1$ | $R^2$ |
|---|---|---|
| 6-Br | H | H |
| 6-trifluoromethyl | H | H |
| 6-methoxy | H | H |
| 6-cyclohexyl | H | H |
| 6-cyclohexyloxy | H | H |
| 6-phenyl | H | H |
| 6-phenoxy | H | H |
| 6-nitro | H | H |
| 6-amino | H | H |
| 6-methylsulfonylamino | H | H |
| 6-(4-chlorophenyl) | H | H |
| 6-(4-chlorophenoxy) | H | H |
| 5-methoxy | H | H |
| 8-methoxy | H | H |

| R | $R^1$ | $R^2$ |
|---|---|---|
| 6-(benzoyl) | H | H |
| 6-(4-chlorobenzoyl | H | H |
| 5-chloro | H | methyl |
| 8-chloro | H | methyl |
| 6-acetyl | H | H |
| H | H | propyl |
| H | H | n-butyl |
| H | H | isopropyl |

Some of the compounds of this genus are known: 2,3-dihydro-N-(2-propenyl)-1,4-benzodioxin-2-carboxamide is disclosed by J. Koo, et al., J. Am. Chem. Soc., 77, 5373 (1955). It, and the others, can be prepared by treating an alkyl, suitably methyl or ethyl, ester of the corresponding carboxylic acid, in solution in a suitable solvent such as ethanol, with 2-propenamine. The reaction will go forward at room temperature; however, higher temperatures — for example, the mixture can be refluxed — may be employed to reduce the reaction time. This procedure is described by Koo, et al. Preferably, about a four-to-six fold excess of the amine is used. The desired product can be recovered by evaporating the solvent and excess amine, then employing conventional techniques, such as selective extraction, recrystallization and/or dry-column chromatography, to isolate the desired product. Use of these procedures in particular instances is illustrated in the working examples included hereinafter.

Alternatively, the amides can be prepared by treating the corresponding carboxylic acid with thionyl chloride, to form the corresponding acid chloride, then treating the acid chloride with the amine. This procedure also is described in the article by Koo, et al. An excess of the thionyl chloride is used, in part acting as solvent. Conveniently, the treatment is conducted by refluxing the mixture. The excess thionyl chloride then is evaporated and the acid chloride is isolated. Alternatively, the crude acid chloride can be treated with an excess of the amine, a solvent such as methylene chloride being added if needed to moderate the reaction and/or to ensure a liquid reaction mixture. The desired product can be recovered from the reaction mixture as indicated above.

The precursor esters wherein $R^1$ = H and $R^2$ = H or alkyl can be prepared as shown by Koo et al, and by F. deMarchi (see Example 3) — i.e., by treating the appropriate catechol

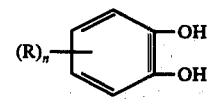

or derivative thereof with the methyl or ethyl ester of the appropriate 2,3-dibromopropionic, -butyric, -pentanoic or -hexanoic acid.

Some of the precursor catechols (R = H, 4-methyl, 4-phenyl, 4-(1,1-dimethylethyl), 3-methoxy) are known compounds; others can be prepared as follows, referring to the substituent, R, n being one, and the position on the catechol ring:

R = 4-Br. Bromination of catechol, with dioxane dibromide, using the procedure of Yanovskaya et al., Zhur. Obschei. Khim. (J. Gen. Chem.) 22, 1594 (1952) (Chemical Abstracts, 47, 8033b).

R = 4-F. The method of Corse et al., J. Org. Chem., 16, 1345 (1951) (Chem. Abst., 46, 6095b).

R = 4-CF$_3$. Treating 3,4-bis(benzyloxy)benzoic acid at 100°–120° C. with phenylsulfur trifluoride (Sheppard, J. Am. Chem. Soc., 84, 3058 (1962); Org. Syn., 44, 39, 82 (1964)), reducing the pressure over the reaction mixture until the product distills and hydrogenating it in the presence of a palladium-on-carbon catalyst.

R = 4-methoxy. Dakin reaction of 2-hydroxy-4-methoxybenzaldehyde according to the procedure of Paulsen, Medd. Norsk Farm. Selskap, 21, 157 (1959) (Chem. Abst. 54, 12481b (1960)).

R = 4-cyclohexyl. Treating catechol with cyclohexene, according to the procedure of Starkov et al., Izv. Vyssh. Ucheb. Zaved. Khim. Khim. Tekhnol., 15, 245 (1972) Chem. Abst. 77, 34072e (1972)).

R = 4-phenoxy. Heating a mixture of 4-iodoveratrol (Janssen et al., J. Org. Chem. 20, 1326 (1955)), sodium phenoxide and a catalytic amount of copper powder at about 200° C. for about 4 hours, then pouring the mixture over ice, extracting the mixture with an organic solvent such as ether, drying the extract, stripping the solvent and distilling the residue to give 4-phenoxycatechol dimethyl ether. Treating this product with an anhydrous aluminum chloride/sodium chloride melt (Janssen et al., supra), pouring the resulting mixture into ice-hydrochloric acid, extracting the mixture with an organic solvent, stripping the solvent under reduced pressure and fractionally distilling the residue gives the desired 4-phenoxycatechol.

R = 4-cyclohexyloxy. Heating a mixture of 4-iodo-1,2-bis-(benzyloxy)benzene, obtained from 1,2-bis(benzyloxy)benzene (Annalen 221, 378) and iodine in the presence of mercuric oxide according to the procedure of Janssen et al., J. Org. Chem. 20, 1326 (1955), sodium cyclohexyloxide (obtained from cyclohexanol and a base such as sodium hydride) and a catalytic amount of copper powder at about 200° C. for about 4 hours, then pouring the mixture over ice, extracting the mixture with an organic solvent such as ether, drying the extract, stripping the solvent and distilling the residue to give 4-cyclohexyoxycatechol dibenzyl ether. Hydrogenating at ethanol solution of this product in the presence of a palladium-on-carbon catalyst followed by filtration to remove the catalyst, stripping of the solvent and vacuum distillation gives the desired 4-cyclohexyloxycatechol.

R = amino. Ethyl 2,3-dihydro-6-nitro-1,4-benzodioxin-2-carboxylate is obtained by the nitration of ethyl 2,3-dihydro-1,4-benzodioxin-2-carboxylate in a water insoluble solvent such as hexane, pentane or petroleum ether with 30% nitric acid at a temperature of 50–60%, followed by fractional crystallization of the product. This, in solution in ethanol, is treated with hydrogen (30 psig) in the presence of a palladium-on-carbon catalyst. The product (R = amino) is recovered by filtering the catalyst, stripping the solvent and recrystallizing the residue.

R = methylsulfonylamino. The R = amino compound (above) is treated with methanesulfonyl chloride in an organic solvent such as toluene, containing an acid acceptor, such as triethylamine or pyridine. The product is isolated by pouring the reaction mixture over ice, filtering the resulting solids from the liquid and recrystallizing the solid material from an organic liquid such as ethanol.

Precursor acids wherein R$^1$ is alkyl can be prepared by treating the appropriate catechol with a 1-chloro-2,3-epoxy-2-alkyl-propane in the presence of aqueous sodium hydroxide at a temperature of about 100° C. to obtain the 2-alkyl-1,4-benzodioxin-2-methanol. This alcohol can be oxidized to the required precursor acid by treatment with Jones reagent (a mixture of chromic anhydride and sulfuric acid). Preferably the alcohol is in solution in a solvent such as acetone and the reagents are mixed at a low temperature such as 5°–10° C., and the mixture is warmed, for example to room temperature, to effect the reaction. This method for preparing these acids illustrated in Example 2, hereinafter; the example also illustrates the manner in which the product acid can be isolated from the reaction mixture and purified.

The procedures for preparing compounds of Formula I are illustrated in Examples 1–4 following. In each case, the identities of the product, and of the precursor(s) involved were confirmed by appropriate chemical and spectral analyses.

Example 1 —
2,3-dihydro-N-(2-propenyl)-1,4-benzodioxin-2-carboxamide (1)

A solution of 5.2 g of the ethyl ester of 2,3-dihydro-1,4-benzodioxin-2-carboxylic acid (Koo et al., supra) and 5.7 g of 2-propenamine in 50 ml of ethanol was refluxed for 20 hours. The solvent was stripped and the residue was treated with charcoal and crystallized from ether-hexane to give 1, as white needles, m.p.: 55.5°–57° (Koo et al.: 59°–61°).

Example 2 —
2,3-dihydro-N-(2-propenyl)-2-methyl-1,4-benzodioxin-2-carboxamide (2)

A mixture of 27.5 g of catechol and 28.3 g of 1-chloro-2,3-epoxy-2-methylpropane (U.S. Pat. No. 3,150,154) in 100 ml of 10% aqueous sodium hydroxide was stirred and refluxed for 4 hours. The mixture then was cooled and extracted with ether. The combined extracts were washed with 5% aqueous sodium hydroxide, dried (MgSO$_4$) and stripped of solvent. The residue was vacuum distilled to give a mixture of 70% 2,3-dihydro-2-methyl-1,4-benzodioxin-2-methanol and 30% 3,4-dihydro-3-methyl-2H-1,5-benzodioxepin-3-ol.

2 g of the mixture was dissolved in acetone and at 10° C. was added dropwise over a 20-minute period 10 ml of 2.7 molar Jones reagent. The resulting mixture was stirred at 10° C. for 1 hour and overnight at room temperature. The mixture then was quenched with water and extracted with ether. The combined ether extracts were washed with water, then extracted with aqueous sodium bicarbonate solution. The combined sodium bicarbonate extracts were acidified with concentrated hydrochloric acid and extracted with ether. The combined ether extracts were washed with water, dried (MgSO$_4$) and stripped of solvent. Recrystallization of the residue from ether-hexane gave 2,3-dihydro-2-methyl-1,4-benzodioxin-2-carboxylic acid (2A).

3.0 g of 2A was dissolved in 15 ml of thionyl chloride and the solution was refluxed for 45 minutes. The excess thionyl chloride was stripped, the residual liquid was cooled with ice, and 20 ml of 2-propenamine was cautiously added. The resulting solution was stirred for 4 hours at room temperature, then the excess amine was stripped off. The residue was partitoned between methylene chloride and water. The organic layer was separated, dried (MgSO₄) and stripped of solvent. The residue was dry column chromatographed through silica gel using Solvent No. 3 (a 4:30:66 by volume mixture of tetrahydrofuran, ethyl acetate and hexane) as eluent, and the product was crystallized from ether-hexane to give 2, as a white solid m.p.: 67°–68°.

Example 3 —
6-chloro-2,3-dihydro-N-(3-propenyl)-1,4-benzodioxin-2-carboxamide (3A) and the 7-isomer (3B) 4-chlorocatechol was condensed with ethyl 2,3-dibromopropionate by the method shown in F. DeMarchi, et al., Gazz. Chim. Ital., 95, 1447–54 (1965). The product was a mixture of isomers: approximately 70% of the 7-chloro-isomer and 30% of the 6-chloro-isomer of the ethyl ester of 2,3-dihydro-1,4-benzodioxin-2-carboxylic acid. A solution of 10 g of the product mixture and 9.1 g of 2-propenamine in 50 ml of ethanol was refluxed for 20 hours. The solvent then was stripped and the resulting gum was dry column chromatographed through silica gel using Solvent No. 3 as eluent. A series of ultraviolet-fluorescent bands in the column were obtained. The bands were isolated by cutting the column at appropriate points. Each separated portion of the column then was extracted with a solvent such as methylene chloride or acetone, each extract was filtered and stripped of solvent. On repeated recrystallization from ether-hexane, one of the residues gave 3A, as a white crystalline solid, m.p.: 72°–73° C., while another gave 3B, as a white crystalline solid, m.p.: 60.5°–61.5° C.

Example 4 —
2,3-dihydro-3-methyl-N-(2-propenyl)-1,4-benzodioxin-2-carboxamide cis isomer (4)

A mixture of diastereoisomeric ethyl esters of 2,3-dihydro-3-methyl-1,4-benzodioxin-2-carboxylic acid, consisting of approximately 67% cis and 33% trans isomers, was prepared from catechol and ethyl 2,3-dibromobutyrate according to the procedure of Koo et al., supra.

A solution of 7.0 g of the mixture of isomers and 14.0 g of 2-propenamine in 100 ml of ethanol was refluxed for 24 hours. Then the solvent was stripped off and the residue was dry column chromatographed through silica gel, using Solvent No. 3 as eluent. Workup by the technique described in Example 3 gave, as one fraction, a yellow liquid, which on repeated recrystallization from ether-hexane gave 4, a white crystalline solid, m.p.: 70.5°–72.5°, identified as the cis isomer by nuclear magnetic resonance spectrum analysis.

Example 5 —
6-(1,1-dimethylethyl)-2,3-dihydro-N-(2-propenyl)-1,4-benzodioxin-2-carboxamide (5)

40 g of ethyl 2,3-dibromopropionate was added slowly to a stirred mixture of 23 g of 4-tertiary-butyl-catechol, 56 g of potassium carbonate and 200 ml of acetone at 25° C. The mixture warmed, then was heated and refluxed for 4 hours. It was then filtered. The solid material was dissolved in water, the solution was extracted with toluene; the toluene extract was combined with the acetone filtrate; then the solvents were evaporated under vacuum and the residue was vacuum distilled, to give a mixture of the ethyl esters of 6- and 7-(1,1-dimethylethyl)-2,3-dihydro-1,4-benzodioxin-2-carboxylic acids (5A), boiling point: 141°–142°, 0.1 Torr.

A mixture of 13.2 g of 5A and 8.5 g of 2-propenamine was held at room temperature for 19 hours. It then was stripped of excess amine under vacuum. The residue was extracted with pentane. On standing overnight, crystals precipitated from the extract. The crystals were collected and recrystallized from hexane to give 5, as a solid, m.p.: 95°–96°.

Example 6 —
2,3-dihydro-6-methyl-N-(2-propenyl)-1,4-benzodioxin-2-carboxamide (6) and its 7-methyl counterpart (7)

15 g of ethyl 2,3-dibromopropionate was added slowly to a stirred refluxing mixture of 24.8 g of 4-methylcatechol, 23 g of potassium carbonate and 250 ml of acetone. In three additional increments was added over a 1-hour period: 20 g of potassium carbonate and 27.2 g of ethyl 2,3-dibromopropionate. The mixture then was refluxed for 6 hours and allowed to stand over a week-end. The mixture then was filtered, the solids were washed with acetone, the solvent was stripped from the combined filtrate and washings and the residue was vacuum distilled to give a mixture of the ethyl esters of 2,3-dihydro-6-(and 7-)-methyl-1,4-benzodioxin-2-carboxylic acids (6A), b.p.: 124°–126.5°, 0.045 Torr.

A mixture of 11.1 g of 6A, 20 g of 2-propenamine and 50 ml of ethanol was stirred at room temperature for 24 hours. The solvent and excess amine were stripped under vacuum. The residue was dry column chromatographed over silica, using a 4:30:50 v/v/v mixture of tetrahydrofuran, ethyl acetate and hexane as eluent. The liquid product was crystallized from ether-hexane. The product was taken up in ether, the solution was cooled and filtered, the solid being product 6B. Upon standing, crystals formed in the mother liquor, and were separated, being product 6C, m.p.: 69–71: 6B was taken up in ether and the solution was cooled, giving crystals, which were separated and recrystallized from ether. The product was recrystallized from pentane-methylene dichloride to give white needles, (6D), m.p.: 76°–79.5°. 6D was designated as the 6--methyl isomer and 6C was designated as the 7-methyl isomer on the basis that the less symmetrical isomer would have the lower melting point.

Example 7 —
7-fluoro-2,3-dihydro-N-(2-propenyl)-1,4-benzodioxin-2-carboxamides (8)

26 g of 4-fluorocatechol (prepared by the procedure of Corse, J. et al., J. Org. Chem., 16, 1345 (1951)) was mixed with 57 g of ethyl 2,3-dibromopropionate at 15°, the temperature of the mixture being allowed to rise over a 2-hour period. The mixture then was refluxed for 3.5 hours, cooled and filtered. The filtrate was stripped of solvent to give a paste, which was filtered. The filtrate was treated with water and then with methylene chloride. The methylene chloride phase was separated and stripped of solvent, and the residue was vacuum distilled to give a mixture of the ethyl esters of 2,3-dihydro-6-(and 7-)-fluoro-1,4-benzodioxin-2-carboxylic acids (8A), b.p.: 116°–120°, 0.1 Torr.

A mixture of 7 g of 8A and 10 g of 2-propenamine was held overnight at room temperature. Then it was stripped of solvent under reduced pressure and the residue was extracted with pentane. The residue then was extracted with cyclohexane, the solvet was stripped under reduced pressure. Th cyclohexane-soluble residue was recrystallized from pentane to give 8, as a solid, m.p.: 54–6°.

The carboxamides of Formula I have been found to inhibit lipogenesis in mammalian tissues. The manner in which they cause this effect is not known with certainty; it is believed that they interfere with the synthesis of fatty acids in the tissues. Their effectiveness for this purpose has been ascertained by immersing samples of mammalian liver or adipose tissue in a liquid medium containing radioactive glucose and the test chemical for a period of time, then isolating the lipid from the treated tissue and determining the up-take of the radioactive carbon by means of scintillation counting techniques. These tests were conducted with both liver and adipose tissues, because in some animals the primary site of lipogenesis appears to be liver tissue, while in others it appears to be adipose tissue. The test animals were pigs, sheep, rabbits, cats and dogs.

Described in more detail, the tests were conducted according to the following general procedure:

Tissue slices (200 milligrams for liver; 150 milligrams for adipose tissue) were incubated, at 37° C. for 2 hours with shaking in 3 milliliters of Krebs-Ringer bicarbonate solution containing one-half the normal calcium ion concentration, 60 micromoles of glucose, 0.5 microCurie of glucose-U-$^{14}$C, 300 microunits of insulin, and 5% dimethyl sulfoxide (DMSO). The test compounds were added as a solution or suspension in DMSO and were present at a concentration of 100 micrograms per milliliter of the incubation mixture.

The incubation was terminated by addition of 0.25 milliliter of 1 N sulfuric acid. The resulting mixture was extracted with a total of 25 milliliters of chloroform:methanol (2:1, v/v). The extracts were washed according to Folch et al. (J. Biol. Chem., 226, 497–509, (1957)), air dried, and counted in a liquid scintillation counter with 15 milliliters of counting fluid (two parts toluene containing 0.4% w/v New England Nuclear Omnifluor: 1 part Triton X-100). The tests were conducted in triplicate and were accompanied by control tests in which all ingredients, proportions and conditions were the same except that no test compound was included. From the data obtained, the percent inhibition of lipid synthesis by the test compound was calculated in each case.

Compound 1 was tested with respect to all of the indicated animal species. The other three compounds were tested only with respect to the pig.

From these and other tests, it has been established that in pigs there is little lipogenic activity in the liver tissue. From these and other tests, it also has been established that swine adipose tissue utilizes glucose for lipogenesis, and to be the major site of fatty acid synthesis. The data obtained from the tests using adipose tissue and glucose are set out in Table 1, as the percent inhibition of lipogenesis compared to the results obtained in the control tests wherein only the test compound was omitted.

TABLE I

| Compound No. | Percent Inhibition |
| --- | --- |
| 1 | 75 |
| 2 | 41 |
| 3 | 64 |
| 3A | 38 |
| 4 | 68 |
| 5 | 36 |
| 6 | 80 |

TABLE I-continued

| Compound No. | Percent Inhibition |
| --- | --- |
| 7 | 55 |
| 8 | 72 |

With respect to sheep, both tissues had relatively low rates of lipogenesis. The liver incorporated more glucose into lipids than did the adipose tissue. Compound 1 inhibited (27%) glucose incorporation in the liver and (50%) in adipose tissue.

With respect to rabbits, compound 1 inhibited (32%) glucose incorporation into liver and (30%) into adipose tissue.

With respect to cats, compound 1 caused 35% inhibition of lipogenesis from glucose in the liver and did not inhibit glucose utilization in adipose tissue.

With respect to dogs, adipose tissue was considerably more active as a lipogenic tissue than was liver tissue. Compound 1 caused 54% inhibition lipogenesis from glucose in adipose tissue.

Compound 1 also was tested to determine the in vivo inhibition of swine adipose tissue lipid synthesis, as follows: pigs weighing about 20 kilograms were administered a fixed drug dose of approximately 25 milligrams of drug per kilogram of animal body weight per day for seven consecutive days. The drug was formulated to contain 10% w active ingredient and was prepared as coarse granules using 4% w plasdene as the granulating agent and lactose as the carrier. Control animals received a comparable amount of lactose as a placebo. The daily drug or placebo dose was added to 1.2 kilograms of swine ration; about one-third of the total was fed at 0800, 1200, and 1600 hours. Biopsy samples were obtained from the dorsal subcutaneous adipose tissue (ca. 1 gram) in the neck region before drug administration, after 7 days of drug administration, and 6 days after withdrawal of drug. Adipose tissue slices were prepared from the biopsy sample, and in vitro lipogenesis was determined with radioactive glucose as substrate. The incubation was similar to that previously described except there was no DMSO or test compound in the flasks. Compared to the control animals, it was found that the test compound had not significantly affected lipogenesis at day 7, but had significantly reduced the lipogenic rate at day 13.

The carboxamides of Formula I can be used to control lipogenesis in mammals such as, for example, pets, animals in a zoo, livestock, fur-bearing animals and domestic animals, including, but not limited to dogs, cats, mink, sheep, goats, swine, cattle, horses, mules and donkeys. The effect is obtained by administering an effective amount of one or a mixture of two or more of the carboxamides orally or parenterally to the animal. They may be administered as such, or as an active ingredient of a conventional pharmaceutical formulation. They may be administered orally by any convenient means. Thus, they may be orally administered as a drench, by intubation, in the animal's food and water, in a food supplement or in a formulation expressly designed for administration of the drug. Suitable formulations include solutions, suspensions, dispersions, emulsions, tablets, boluses, powders, granules, capsules, syrups and elixirs. For parenteral administration, they may be in the form of a solution, suspension, dispersion or emulsion. They can be administered in the form of an implant or other controlled sustained release formulation. Inert carriers, such as one or more of water, edible oil, gelatin, lactose, starch, magnesium stearate, talc or vegetable gum can be used. The dosage of the carboxamide needed to inhibit lipogenesis will depend upon the particular carboxamide used, and the particular animal being treated. However, in general, satisfactory results are obtained when the carboxamide is administered in a dosage of from about 1 to about 500 milligrams per kilogram of the animal's body weight. The carboxamide can be administered in a single dose or in a series of doses in the same day, or over a period of days. For any particular animal, a specific dosage regimen should be adjusted according to the individual need, the particular carboxamide(s) used as the inhibitor, and the professional judgement of the person administering or supervising the administration of the inhibitor. It is to be understood that the dosages set forth herein are exemplary only, and that they do not, to any extent, limit the scope or practice of the invention.

I claim:

1. A method of inhibiting lipogenesis in a mammal, which comprises administering, to a mammal in need of such treatment, orally or parenterally an effective amount of a compound of the formula:

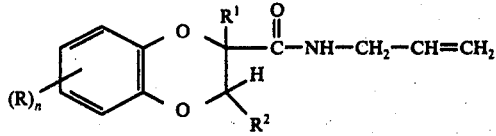

wherein $n$ is zero or one, R is halogen; nitro; amino; methylsulfonylamino; trifluoromethyl; alkyl or alkoxy of from one to six carbon atoms; cycloalkyl or cycloalkyloxy of from three to six carbon atoms; phenyl or phenoxy, or either of these substituted by one or two of one or more of alkyl of from one to six carbon atoms, halogen and nitro, and $R^1$ and $R^2$ each is hydrogen or alkyl of from one to four carbon atoms, at least one being hydrogen.

2. A method according to claim 1 wherein R, $R^1$ and $R^2$ each is hydrogen.

* * * * *